(12) United States Patent
Burke et al.

(10) Patent No.: US 9,707,134 B1
(45) Date of Patent: Jul. 18, 2017

(54) SANITARY DEVICE

(71) Applicants: Thomas J. Burke, Whitehouse Station, NJ (US); Jack V. Fullman, Hopatcong, NJ (US)

(72) Inventors: Thomas J. Burke, Whitehouse Station, NJ (US); Jack V. Fullman, Hopatcong, NJ (US)

( * ) Notice: Subject to any disclaimer, the term of this patent is extended or adjusted under 35 U.S.C. 154(b) by 0 days.

(21) Appl. No.: 13/728,267

(22) Filed: Dec. 27, 2012

(51) Int. Cl.
*A61F 13/471* (2006.01)
*A61F 13/512* (2006.01)
*A61F 13/491* (2006.01)

(52) U.S. Cl.
CPC ........ *A61F 13/471* (2013.01); *A61F 13/4915* (2013.01); *A61F 13/512* (2013.01); *A61F 13/5121* (2013.01)

(58) Field of Classification Search
CPC .......... A61F 2013/15146; A61F 13/471; A61F 13/512; A61F 13/5121; A61F 13/4915
USPC ........... 604/346–355, 378–383, 385–385.19; 2/403, 400
See application file for complete search history.

(56) References Cited

U.S. PATENT DOCUMENTS

| 4,847,134 A | * | 7/1989 | Fahrenkrug et al. | .......... 428/138 |
| 6,129,718 A | * | 10/2000 | Wada | ............................ 604/378 |
| 2004/0122396 A1 | * | 6/2004 | Maldonado | ........... A61F 13/512 |
| | | | | 604/383 |
| 2006/0282055 A1 | * | 12/2006 | Shiomi | ............... A61F 13/4915 |
| | | | | 604/385.09 |
| 2008/0027404 A1 | * | 1/2008 | Hernandez et al. | ..... 604/385.06 |

* cited by examiner

*Primary Examiner* — Leslie Deak
*Assistant Examiner* — Kai Weng
(74) *Attorney, Agent, or Firm* — Joanne M Martin

(57) ABSTRACT

An easily applied and replaced flexible container pouch applied to the penis end and including a restricted opening collar to grasp the penis shaft. The container pouch comprises a plurality of walls having a fluid absorbent layer between at least 2 walls, the inner wall (proximal to the penis) include apertures allowing the fluid emitted by the penis to be received into the absorbent layer(s). In one embodiment, the inner layer(s) comprise fluid barriers (e.g. fluid impermeable or a thick member providing a mechanical spacing) between the fluid-filled absorbent layer(s) and the penis. The resulting device provides comfort and protection from unnecessary fluid immersion and ease of use, application and replacement.

7 Claims, 1 Drawing Sheet

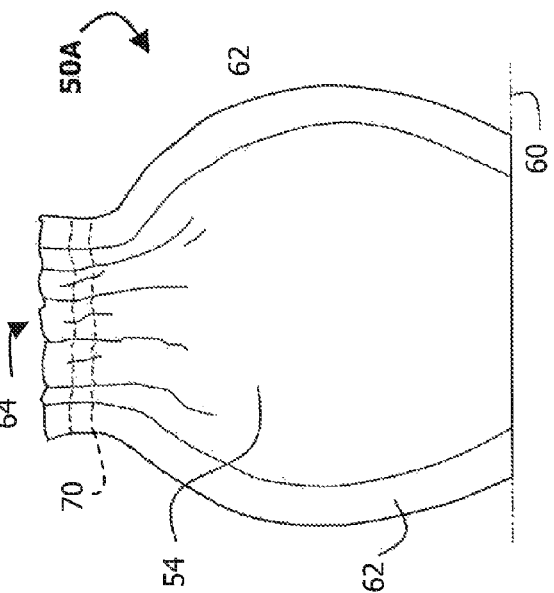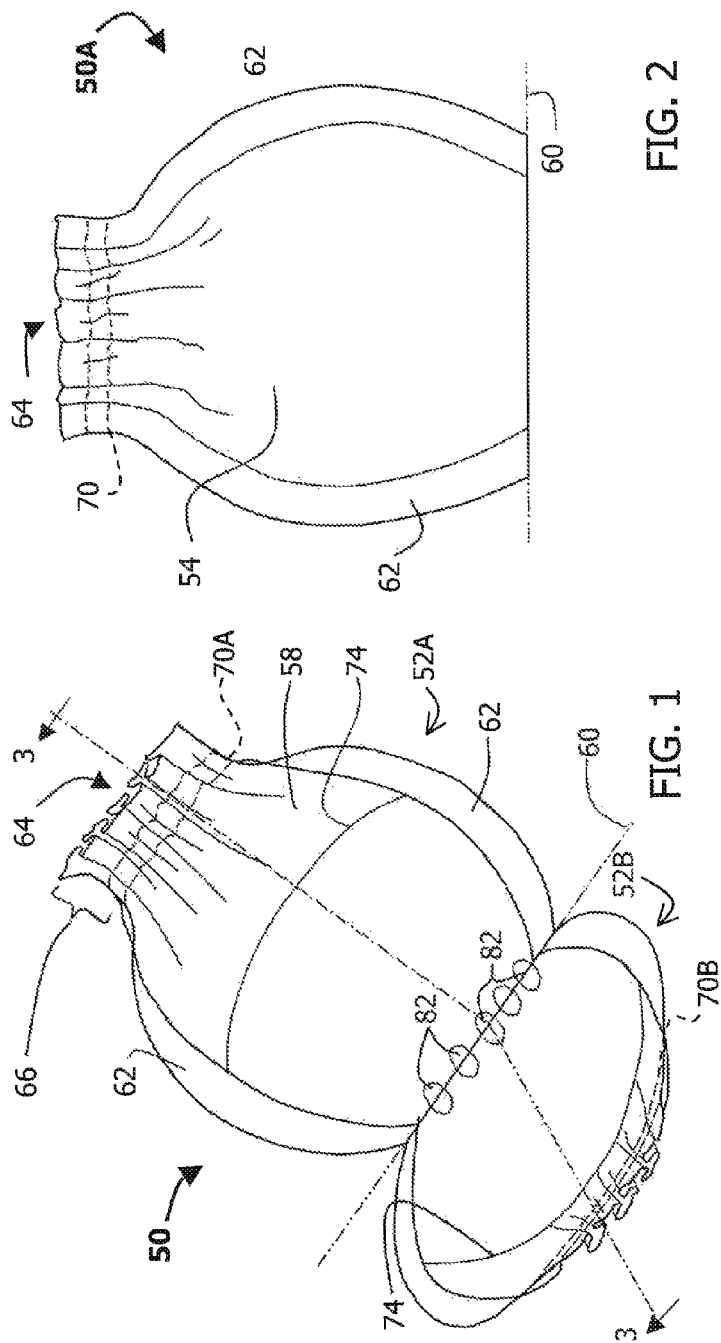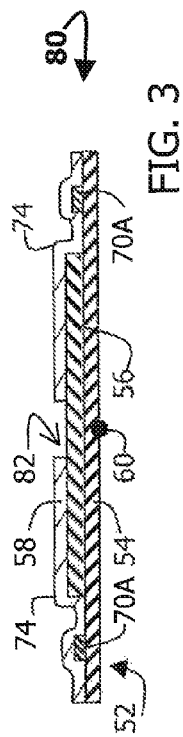

SANITARY DEVICE

FIELD OF THE INVENTION

The present invention relates to devices for retaining emissions of bodily fluids, in particular to devices for retaining penile emissions of urine.

BACKGROUND OF THE INVENTION

Unwanted penile emissions of urine are often merely drained away, or absorbed. However, a draining apparatus often requires multi-section apparatus having elements separately located and complex or difficult to use connecting elements, which may leak or restrict freedom of user movement. Absorbing devices may also be difficult to apply and continue to subject a portion of the penis in the emitted urine or other fluid, especially if the device is intended to store a significant quantity of emitted fluid.

SUMMARY OF THE INVENTION

The apparatus according to the present invention provides an easily applied and replaced flexible container pouch applied to the penis end and including a restricted opening collar to grasp the penis shaft. The container pouch comprises a plurality of walls having a fluid absorbent layer between at least 2 walls, the inner wall (proximal to the penis) include apertures allowing the fluid emitted by the penis to be received into the absorbent layer(s). In one embodiment, the inner layer(s) comprise fluid barriers (e.g. fluid impermeable or a thick member providing a mechanical spacing between the penis and the absorbent layer) between the fluid-filled absorbent layer(s) and the penis. The resulting device provides comfort and protection from unnecessary penis fluid immersion and ease of use, application and replacement.

BRIEF DESCRIPTION OF THE DRAWING

These and further features according to the present invention will be better understood by reading the following Detailed Description taken together with the Drawing figures, wherein:

FIG. 1 is a perspective view of an exemplary embodiment of the present invention having two mating sections separated to reveal internal arrangements;

FIG. 2 is a vertical plan view of the embodiment of FIG. 1; and

FIG. 3 is a cross-section view of the multi-layer wall structure according to the embodiment of FIG. 1.

DETAILED DESCRIPTION

A perspective view 50 of one embodiment according to the present invention is shown in FIG. 1, wherein a volumetric fluid container is formed by two complementary and facing walls 52A and 52B at least one being pliant, and in the particular embodiment 50 of FIG. 1, they are different portions of a common outer member (54 of FIG. 3) which is folded along an edge line 60 and have a peripheral margin 62 which peripheral margin when the embodiment is folded, faces and is sealed with another portion 66 of the peripheral margin to form an volumetric area between the facing walls 52A and 52B totally enclosed except for a region 64 which remains unsealed between the walls 52A and 52B to form an opening between the walls 52A and 52B periphery wherein a penis may be introduced into the volumetric region formed between the more central regions of walls 52A and 52B. The portion 66 of the periphery 62 of the walls 52A and 52B which form the opening is preferably gathered around the shaft of the penis to support and retain the sanitary device 50 thereon, and may be provided by an elastic element 70A disposed between the layers 54 and 58, on the surface thereof 70B, or part of the material of the layers, to gather (fold upon itself) the margin 62.

An interior layer 58 is disposed on the outer layer 52 as shown in the cross-sectional view 80 of FIG. 3 with an absorbent layer 56 disposed therebetween. In one embodiment, the inner layer 58 comprises a substantially planar, fluid impermeable layer which when the absorbent layer 56 is fluid-laden to keep the fluid apart from a penis as inserted into the opening 64 to the volumetric area therein. Alternate embodiments provide an inner surface that are not planar but varied in disposition, e.g. corrugated, folded, irregular surfaces, which also maintains separation between the penis and the fluid-laden absorption layer 56, and may further include spaces within surface 58 wall to permit a flow of fluid away from the penis. In the particular embodiment shown, the absorbent layer 56 extends only partially along the walls 52 and 58 from the fold 60 to the opening region 64, as indicated by the transition line 74. In one embodiment, the inner layer includes one or more apertures 82 disposed on the distal end located proximal to the fold line 60 and opposite said the opening region 64 and through which fluid emitted from penis is communicated to the absorbent layer 56. Typically, the fluid received is then moved away from the aperture(s) 82 generally toward a distal part of the absorbent layer, e.g. near transition line 74, and isolated from the penis by the inner wall 58 except via aperture(s) 82.

An elevational view 50A of the exemplary embodiment is shown in FIG. 2, wherein the outer surface member 54 is folded at 60 and the periphery 62 is sealed except in the region 64 wherein the opening is formed to receive the penis.

Alternate embodiments may include a plurality of inner layers for augmented fluid absorption where they may individually or together communicate to the inner volume to receive the emitted fluid, and further alternative structures disposed to retain portion 66 about the penis shaft. Further modifications and substitutions according to one skilled in the art are within the scope of the present invention, which is not limited except by the claims that follow.

What is claimed is:

1. A sanitary device, comprising:
   a pliant first wall and a substantially confronting pliant second wall each having a periphery and being relatively sealable at said periphery to form an expandable volume configured to receive a male penis and fluids emitted therefrom between said first wall and said second wall, at least one of said first wall and said second wall comprising a plurality of layers including a fluid impermeable outer wall, an absorbent layer disposed relatively inward from said outer wall, and a relatively inwardly disposed wall inhibiting direct contact with said absorbent layer from within said volume, wherein
   said first wall and said second wall are sealed along a major portion of said periphery leaving along a region of said periphery, an opening into said volume between said first wall and said second wall along said periphery, said relatively inwardly disposed wall is fluid impermeable except for least one aperture disposed on a distal end opposite said opening into said volume providing fluid communication between said volume and said absorbent layer, isolating fluid retained in said absorbent layer from within said volume except via said at least one aperture, and wherein said region of said periphery includes an expandable region of said periphery.

2. The sanitary device of claim 1, wherein said first wall and said second wall are formed from a single member foldable towards each other and itself to form a gathered region along a portion of said periphery.

3. The sanitary device of claim 1, wherein said expandable region of said periphery configured to gather said outer wall around a penis inserted into said volume.

4. The sanitary device of claim 1, wherein said expandable region comprises a resiliently expandable region favoring a minimal expansion thereof.

5. The sanitary device of claim 1, wherein said relatively inwardly disposed wall membrane comprises a substantially non-planar wall membrane.

6. A sanitary device, comprising:

a pliant first wall and a substantially confronting pliant second wall each having a periphery and being relatively sealable at said periphery to form an expandable volume between said first wall and said second wall, at least one of said first wall and said second wall comprising a plurality of layers including a fluid impermeable outer wall, an absorbent layer disposed relatively inward from said outer wall, and a relatively inwardly disposed wall inhibiting direct contact with said absorbent layer from within said volume, wherein said first wall and said second wall are sealed along a major portion of said periphery leaving along a region of said periphery, an opening into said volume between said first wall and said second wall along said periphery, and said relatively inwardly disposed wall is fluid impermeable except for at least one aperture disposed on a distal end opposite said opening into said volume providing fluid communication between said volume and said absorbent layer, isolating fluid retained in said absorbent layer from within said volume except via said at least one aperture.

7. The sanitary device of claim 6, wherein said relatively inwardly disposed wall including a wall membrane.

\* \* \* \* \*